United States Patent [19]

Avery et al.

[11] Patent Number: 5,225,554
[45] Date of Patent: Jul. 6, 1993

[54] POLYOXA TETRACYCLIC COMPOUNDS

[75] Inventors: Mitchell A. Avery, Palo Alto; Clive Jennings-White, Mountain View, both of Calif.

[73] Assignee: SRI International, Menlo Park, Calif.

[21] Appl. No.: 554,333

[22] Filed: Jul. 18, 1990

Related U.S. Application Data

[60] Division of Ser. No. 312,376, Feb. 15, 1989, Pat. No. 4,963,683, which is a continuation of Ser. No. 943,555, Dec. 18, 1986, abandoned.

[51] Int. Cl.$^5$ .................. C07D 313/06; C07D 313/00; C07D 273/00
[52] U.S. Cl. ..................... 540/520; 540/581; 546/63; 549/24; 549/25; 549/268; 549/276; 549/348; 549/358
[58] Field of Search .................. 549/12, 15, 263, 268, 549/279, 348, 358, 24, 25, 276, 352, 367; 546/63, 64; 540/581, 520

[56] References Cited

U.S. PATENT DOCUMENTS

| | | | |
|---|---|---|---|
| 4,350,638 | 9/1982 | Lee | 549/275 |
| 4,963,683 | 10/1990 | Avery et al. | 546/63 |
| 5,011,951 | 4/1991 | Buchs et al. | 549/348 |
| 5,019,590 | 5/1991 | Avery et al. | 549/276 |

FOREIGN PATENT DOCUMENTS

| | | | |
|---|---|---|---|
| 0330520 | 8/1989 | European Pat. Off. | 549/348 |
| 0362730 | 4/1990 | European Pat. Off. | 549/348 |

OTHER PUBLICATIONS

Lee et al., *Tetrahedron Letters* (Mar. 1973) No. 12, pp. 965-968.
Rosch et al., *Organomet. Chem.* (1980) 195:47-53.
Trost et al., *J. Amer. Chem. Soc.* (1983) 105:4494-4496.
Rosch et al., *Angew. Chem. Int. Ed. Engl.* (1981) 20:581-582.
Desjardins et al., *Antimicrob. Agents Chemother.* (1979) 16(6):710-718.
Milhous et al., *Antimicrob. Agents Chemother.* (1979) 27(4):525-530.
Roush et al., *J. Amer. Chem. Soc.* (1984) 106:721-723.
Claus et al., *Org. Syn.* (1985) 64:150-156.
Imakura et al., *J. Chem. Soc. Chem. Commun.* (1988) pp. 372-374.

(List continued on next page.)

*Primary Examiner*—C. Warren Ivy
*Assistant Examiner*—Raymond Covington
*Attorney, Agent, or Firm*—Richard P. Lange; Morrison & Foerster

[57] ABSTRACT

A process for synthesizing polyoxa tetracyclics which involves the ozonolysis of a single-ring-structure vinyl silane with resulting direct formation of the desired multiple ring material. The polyoxa tetracyclic compounds have the formula

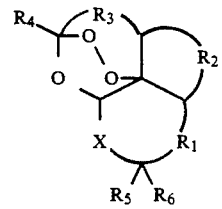

The vinyl silanes have the structure

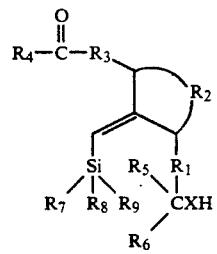

The vinyl silanes are new chemical compounds as are corresponding primary ozonide and dioxetane intermediates. In a preferred embodiment, this invention provides a total synthesis of the antimalarial artemisinin.

8 Claims, 8 Drawing Sheets

OTHER PUBLICATIONS

Bates et al., *J. Organ. Chem.* (1989) 54:1784–1785.
Merk Index, 9th Edition pp. 7853–7854.
G. Schmid et al., *Journal of the American Chem. Soc.* 103:(3) 624–5 (1983).
Wei Shan Zhou, *Pure and Applied Chem.* 58:817–24 (1986).
Buchi et al., *Journal of the American Chem. Soc.* 100:(1), 294–5 (1978).
Klayman, D. L., *Science* 228:1049–55, (1985).
Klayman, D. L., *Chinese Medial Journal* 92:(#12) 811–16, (1979).
PCT Patent Application PCT/US87/03330 (Dec. 15, 1987).
Katsuhara, *J. Organ. Chem.* (1967) 32(3):797–799.
Caine et al., *J. Organ. Chem.* (1984) 49:2647–2650.
Oppolzer et al., *Helv. Chim. Acta* (1978) 61:2755–2762.
Stowell et al., *Org. Synthesis* (1984) 62:140–148.
Brossi et al., *J. Med. Chem.* (1988) 31:645–650.
Francotte et al., *Helv. Chim. Acta* (1987) 70:1569:1582.

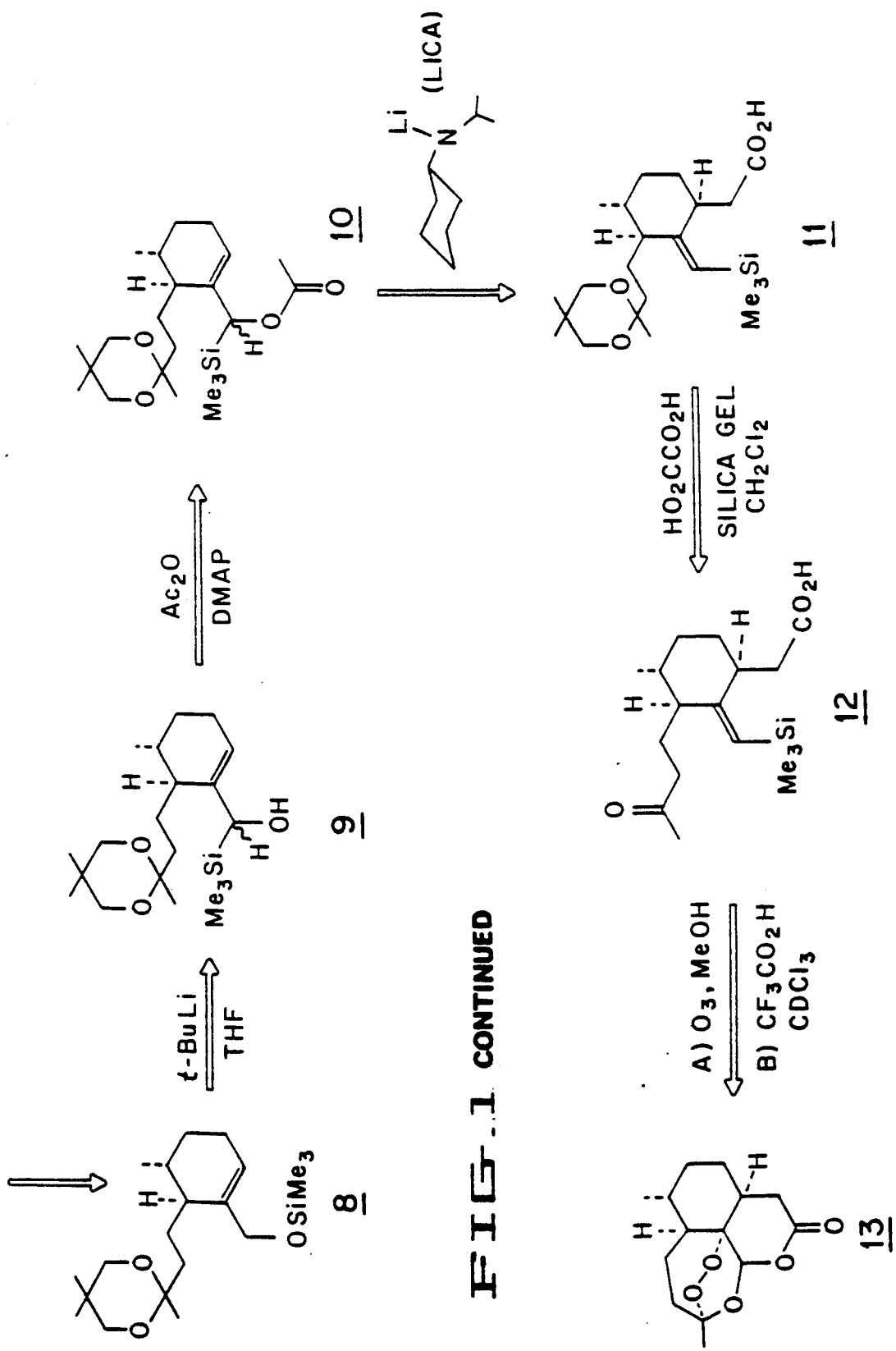
FIG._1 CONTINUED

POLYOXA TETRACYCLIC COMPOUNDS

This invention was made during the performance of a contract from the United States government Department of the Army. The United States government has rights under this invention.

This application is a division of application Ser. No. 07/312,376, now U.S. Pat. No. 4,963,683, filed Feb. 15, 1989, which is a continuation of Ser. No. 06/943,555, filed Dec. 18, 1986, now abandoned.

BACKGROUND OF THE INVENTION

1. Field of the Invention

This invention is in the field of organic chemistry. More particularly it relates to a steroselective synthesis of oxygen-containing heterocyclic organic compounds and materials formed by this process. In one application, this process is used to prepare the antimalarial agent known as qinghaosu or arteminisin.

2. Background References

There are two distinct bodies of art of interest. One is the art relating to the chemical reactions employed in the steroselective synthesis. The other is the art relating to antimalarials to which this process can advantageously be applied.

A key step in the chemical synthesis is the ozonolysis of a vinylsilane which leads transiently to an α-hydroperoxyaldehyde, and thence to the desired product. The only reference of which we are aware which involves ozonolysis of a vinylsilane and can lead to an α-hydroxyperoxyaldehyde is that of George Buchi, et al, *Journal of the American Chemical Society*, Vol 100:1, 294 (1978). This reference illustrates the use of this reaction but arrives at different ring structures than called for herein.

The antimalarial qinghaosu has been used in China in the form of crude plant products since at least twenty years, there has been an extensive interest in this material. This has led to an elucidation of its structure as

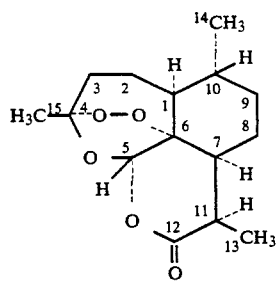

The chemical name arteminisin has been applied to the material. This name will be used in this application to identify the material.

The carbons in the arteminisin structure have been numbered as set forth above. When reference is made to a particular location in a tetracyclic compound of this general type it will, whenever possible, be based on the numbering system noted in this structure. For example, the carbon atoms bridged by the peroxide bridge will always be identified as the "4" and "6" carbons, irrespective of the fact that this invention can involve materials having different bridge length structures in which these carbons would properly be otherwise numbered.

References to arteminisin and to some derivatives of it include the May 31, 1985 review article by Daniel L. Klayman appearing in *Science*, Vol 228, 1049, (1985); and the article appearing in the *Chinese Medical Journal*, Vol 92, No. 12, 811 (1979). Two syntheses of arteminisin have been reported in the literature by Wei-Shan Zhou, *Pure and Applied Chemistry*, Vol 58(5), 817, (1986); and by G. Schmid et al, *Journal of the American Chemistry Society*, Vol 105(3), 624 (1983). Neither of these syntheses employs the ozonolysis as set forth herein.

The interest in arteminisin has prompted a desire for an effective and efficient method for its total synthesis so as to eliminate the need to recover the material from crude vegetable preparations. A total synthesis method will also permit this family of compounds to be radiolabeled in nonlabile positions. This invention serves to satisfy these needs.

STATEMENT OF THE INVENTION

A new process for stereoselectively synthesizing multiple ring compounds having a plurality of ring oxygens has now been discovered. This process involves the ozonolysis of a single-ring-structure vinyl silane with resulting direct formation of the desired multiple ring material. More particularly, the process is directed to the preparation of polyoxa tetracyclic compounds of the following General Formula I.

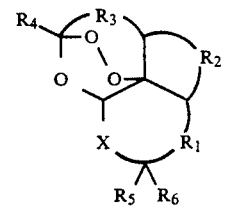

In Structure I., X is a heteroatom bridge selected from $-O-$, $-S-$, and

;

$R_1$ is an organic bridge which can be a methylene ($-CH_2-$) unit or a two or three carbon atom long chain with or without substituents; $R_2$ is an organic bridge which can be a covalent single bond or a methylene unit through five carbon atom long chain with or without substituents; $R_3$ is an organic bridge which can be a methylene unit through three carbon chain with or without substituents; $R_4$ is a hydrogen or an alkyl group, with or without substituents; $R_5$ and $R_6$ can together be a carbonyl oxygen or $R_5$ can be a hydrogen, an alkyl or a substituted alkyl while $R_6$ is a hydrogen, a hydroxyl, an alkyl ether, a carboxylic ester, a carbonate, a carbamate, an amide, or a urea, and $R_{10}$ is a hydrogen or an alkyl or aryl with or without substituents.

The stereoselective synthesis process of this invention includes as a key step, subjecting to ozonolysis a vinylsilane compound of General Formula II.

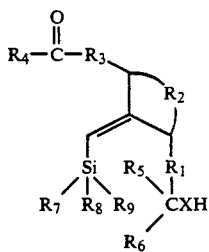

II.

In General Formula II., $R_1$ through $R_6$ and X are as defined with the polyoxa tetracyclic compounds of General Formula I and $R_7$, $R_8$ and $R_9$ are independently selected from lower hydrocarbyls.

In additional aspects, this invention involves the vinyl silanes of General Formula II, as new chemical compounds and primary ozonides or molozonides of General Formula III, and dioxetanes of General Formula IV, as new intermediates.

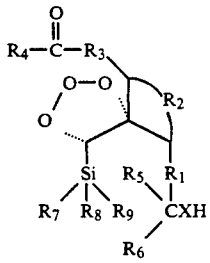

III.

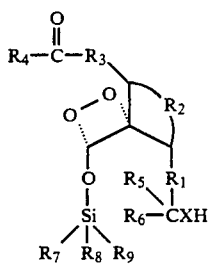

IV.

In General Formulas III, and IV, the various Rs and X have the same identities set out with Formulas I, and II.

In additional and more specific aspects, this invention provides a method for synthesizing arteminisin by ozonolysis of the correspondingly substituted vinylsilane, 17.

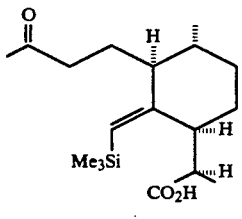

17

DETAILED DESCRIPTION OF THE INVENTION

DESCRIPTION OF PREFERRED EMBODIMENTS

Figure 1:
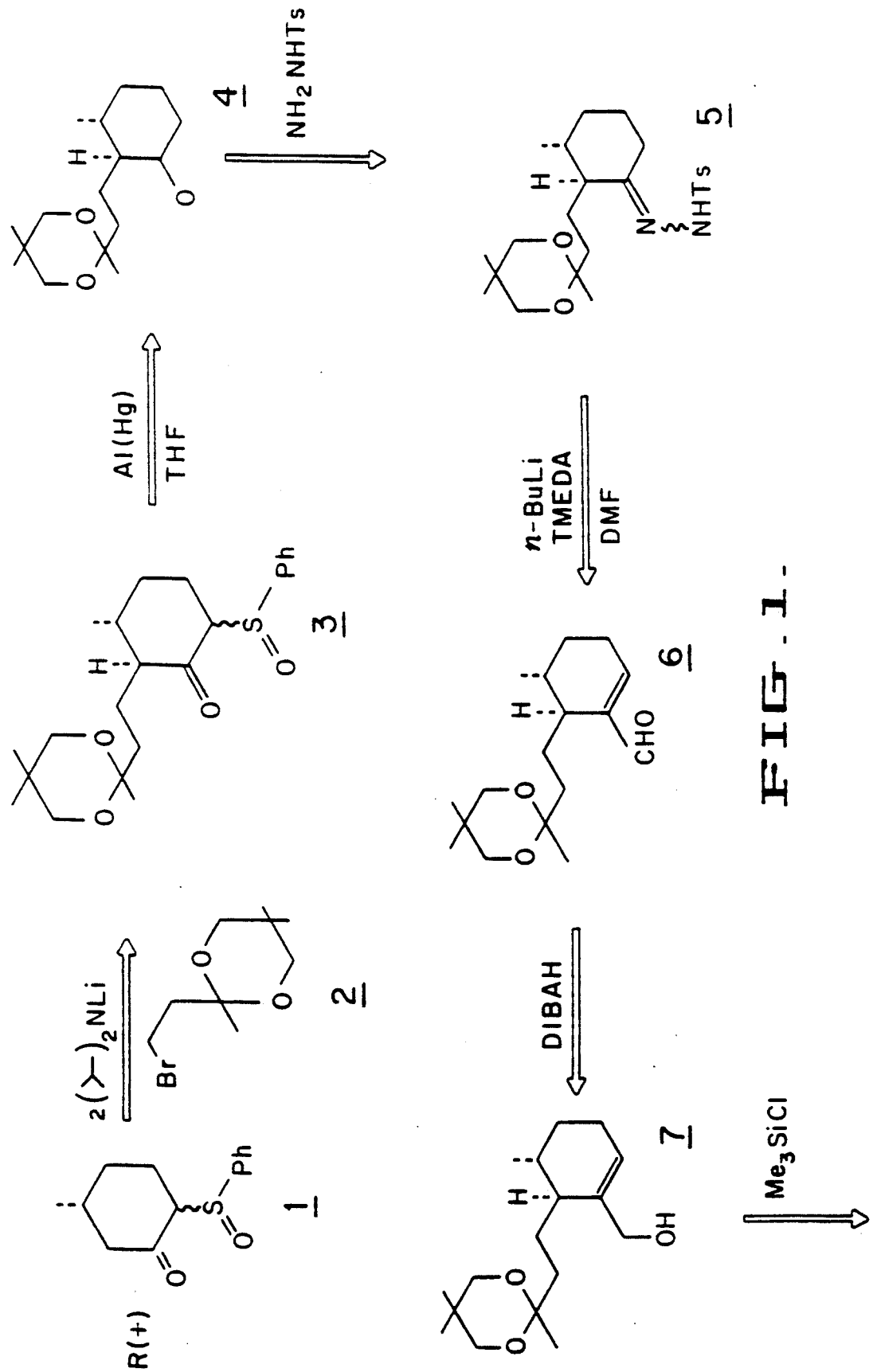
FIG. 1 is a flow diagram showing a sequence of chemical reactions which result in the total synthesis of an arteminisin analog.

In accord with this invention, polyoxa tetracyclic compounds of General Formula I. are prepared by ozonolysis of the vinyl silanes of General Formula II. which reaction proceeds through primary ozonides of General Formula III. and dioxetanes of General Formula IV. as intermediates. This *Description of Preferred Embodiments* relating to this invention is arranged in the following sections:

The Polyoxya Tetracyclic Compounds
The Vinyl Silanes
The Intermediates
The Ozonolysis Reaction
The Incorporation of the Ozonolysis into an Overall Synthesis Scheme
Examples 1. The Polyoxa Tetracyclic Compounds The polyoxa tetracyclic compounds which are prepared by the process of this invention can be defined structurally by means of General Formula I. In defining the groups represented by the various R's in General Formula I, and likewise in General Formulas II., III. and IV., reference is made to the possibility of "substituting" these groups. The limits of this possible substituting can be spelled out in functional terms as follows: A possible substituent is a chemical group, structure or moiety which, when present in the compounds of this invention, does not substantially interfere with the preparation of the compounds or which does not substantially interfere with subsequent reactions of the compounds. Thus, suitable substituents include groups that are substantially inert at the various reaction conditions presented after their introduction such as the ozonolysis and acidification. Suitable substituents can also include groups which are predictably reactive at the conditions to which they are exposed so as to reproducibly give rise to desired moieties.

These possible substituents will from time to time be referred to as $R^*$ such that $R_1$, $R_2$ or the like will be described as including one or more $R^*$ substituents. $R^*$ can be any substituent meeting the above functional definition. Common $R^*$ groups include saturated aliphatic groups including linear and branched alkyls of 1 to 20 carbon atoms such as methyl, ethyl isopropyl, n-butyl, t-butyl, the hexyls including cyclohexyl, decyl, hexadecyl, eicosyl, and the like. $R^*$ can also include aromatic groups generally having from 1 to 20 aromatic carbon atoms, for example aryls such as quinolines, pyridines, phenyls, naphthyls, and aralkyls of up to about 20 total carbon atoms such as benzyls, phenylethyls and the like, and alkyls of up to about 20 total carbon atoms such as the xylyls, ethylphenyls and the like. These various hydrocarbon structures of the $R^*$ substituents may themselves include olefinic carbon-carbon double bonds, subject to the understanding that the ozonolysis may attack and oxidatively cleave this unsaturation if it is present during that reaction, amides, sulfonates, carbonyls, carboxyls, alcohols, esters, ethers, sulfonamides, carbamates, phosphates, carbonates, sulfides, sulfhydryls, sulfoxides, sulfones, nitro, nitroso, amino, imino, oximino, α-, β-unsaturated variations of the above, and the like, subject to the understanding that many of these functional groups may be subject to attack during the overall reaction sequence and thus may need to be appropriately protected. They can then be deprotected at some later stage as desired.

The R* group will also be read in defining certain "X" groups.

In General Formula I., $R_1$ is an organic bridge joining the "7" and "12" carbon atoms. As used herein, the term "organic bridge" denotes a covalent bridge. The $R_1$ bridge can be a methylene (—CH$_2$—) unit or a two or three carbon atom long alkylene chain, (—CH$_2$—CH$_2$—, or —CH$_2$—CH$_2$—CH$_2$—) with or without R* substituents. When $R_1$ is substituted, the substituents replace hydrogens. When there are more than one such substituent they can be on different carbons or there can be two substituents on the same carbon. In certain preferred embodiments, $R_1$ is a one or two carbon alkylene, that is a methylene or an ethylene, with or without one or more, e.g. one or two lower alkyl R* substituents. As used herein, the term "lower" when used as a qualifier or organic group size denotes an organic group of from one to ten carbons and, unless otherwise noted, includes both linear and branched materials. More preferably it is a one carbon alkylene, especially with a single lower alkyl substituent, particularly with a methyl substituent.

The $R_2$ bridge can be a covalent single bond between the "1" and "7" carbons or a one carbon atom through five carbon atom long alkylene chain, that is a —(CH$_2$)$_{n=1-5}$—, between these two carbons with or without R* substituents. When there are more than one R* substituents they can be on different carbons or there can be two substituents on the same carbon of the chain. R* substituents, if present on the $R_2$ bridge, preferably are selected from alkyls, especially lower alkyls, such as methyl, ethyl, propyl, butyl, and the like. More preferred $R_2$ groups are three through five atom long alkylene bridges having from zero through two alkyl substituents. Three atom long alkylene bridges with such substituents are the most preferred $R_2$s.

$R_3$ is a one carbon atom through three carbon atom long alkylene chain, that is a —(—CH$_2$)$_{n=1-3}$—, between the "1" and "4" carbons. The carbon atom of the $R_3$ chain which is adjacent to the "4" carbon can be substituted with one or two R* groups when $R_3$ is two or three carbon atoms long. Preferred R* groups for substituenting $R_3$ are lower alkyls. Preferred $R_3$ groups are the one or two carbon atom long alkylenes with two carbon atom long alkylenes being most preferred.

$R_4$ is a hydrogen, a methyl or a methyl substituted with an R*. Methyl and methyl substituted with a lower alkyl are preferred $R_4$ groups with methyl being the most preferred $R_4$ group.

$R_5$ and $R_6$ can together be a carbonyl oxygen attached to the "12" carbon position. Alternatively, $R_5$ can be a hydrogen, a methyl or an R*-substituted methyl while $R_6$ is a hydrogen, a hydroxyl, or an alkyl—preferably lower alkyl—ether, an ester formed by the hydroxyl with a carboxylic acid of the formula HOOC—CH$_3$ or HOOC—CH$_2$R* (i.e. acetic acid or a substituted acetic acid), a carbonate, a carbamate, an amide, or a urea. The carbonyl configuration appears in the desired arteminisin product, and thus is preferred.

When $R_6$ is hydroxyl, hydrogen, methyl and lower alkyl-substituted methyl are preferred $R_5$ groups.

X is a heteroatom bridge selected from —O—, —S—, and

When X is

$R_{10}$ can be selected from hydrogen, and R* and thus can include alkyls, with and without substituents, as well as directly coupled aryls, with or without substituents. The preferred X groups are —O—, —S—,

and

wherein $R_{10}$ is a lower alkyl. The most preferred X is —O—.

2. The Vinyl Silanes

The vinyl silanes from which the polyoxa tetracyclics are prepared are novel compounds represented by General Formula II. In General Formula II., $R_1$ through $R_4$ and X have the meanings set forth above with reference to General Formula I., $R_5$ and $R_6$ are a carbonyl oxygen and the three $R_7$, $R_8$ and $R_9$ groups in the silyl functionality are independently selected from lower hydrocarbyls. Typical hydrocarbyls for this application are lower alkyls, aryls, alkyls and aralkyls. In selecting these three R's, generally two or three of them are methyls. Typical silyl groups include trimethyl silyl, t-butyl dimethyl silyl and phenyldimethyl silyl. In preferred silyls $R_7$ and $R_8$ are each methyls and $R_9$ is a methyl, ethyl, propyl, butyl, or t-butyl.

3. The Intermediates

In the practice of the present invention, the above noted vinyl silanes are subjected to ozonolysis to ultimately yield the desired tetracycles. In this ozonolysis, two transitory intermediates are formed. These materials are primary ozonides or molozonides of General Formula III, and dioxetanes of General Formula IV. In these intermediates, the various $R_1$ through $R_9$ groups have the meanings and preferences described with reference to Formulas I, and II.

4. The Ozonolysis Reaction

The process of this invention employs an ozonolysis reaction in its formation of the desired polyoxa tetracyclics. This reaction is carried out at low temperatures in a liquid reaction medium. Ozone is extremely reactive and it is advantageous to employ low temperatures to avoid side reactions between the ozone and other regions of the vinyl silane molecule. The low temperature can range from a high of about 15° to a low equal to the freezing point of the reaction solvent, which can be as low as −100° C. or lower. Excellent results are obtained at dry ice/acetone bath temperatures (−78° C.) and a preferred temperature range is from −100° C. to about −25° C. with most preferred temperatures being in the range of from −70° C. to −80° C.

The reaction solvent employed in this reaction is selected to assure compatibility with the highly reactive ozone. As a general rule, ethers, both linear and cyclic, are to be avoided as they are likely to be converted to peroxides which present an explosion hazard. The solvents employed are polar organics, preferably lower alcohols such as methanol, ethanol, the propanols and ethylene and propylene glycols; lower ketones such as acetone and methyl-ethyl ketone; and the and liquid esters such as ethyl acetate. Of these solvents, the lower alcohols, and especially methanol, are preferred.

The reaction is carried out by mixing the vinyl silane in the reaction medium and then adding the ozone. The amount of ozone preferably is controlled so that excesses are avoided. Good results are obtained when the amount of ozone is limited to not more than 1.25 equivalents, based on the amount of vinyl silane present, with ozone levels of from about 0.75 to about 1.25 equivalents based on the amount of vinyl silane present being preferred. Lower ozone levels can be used, but are not preferred because of the lower yields which result from them.

The reaction is very quick, being complete in a few minutes at most. Excellent results are obtained at times in the range of 15 seconds to about 15 minutes. As will be noted below, it is advantageous to limit this reaction period.

The ozonolysis reaction product contains the above-described dioxetane. This material appears to have been formed by rearrangement of the transitory molozonide also described above. This reaction sequence can be illustrated by the following formula which is based on the materials employed in the preferred application of this process to prepare arteminisin:

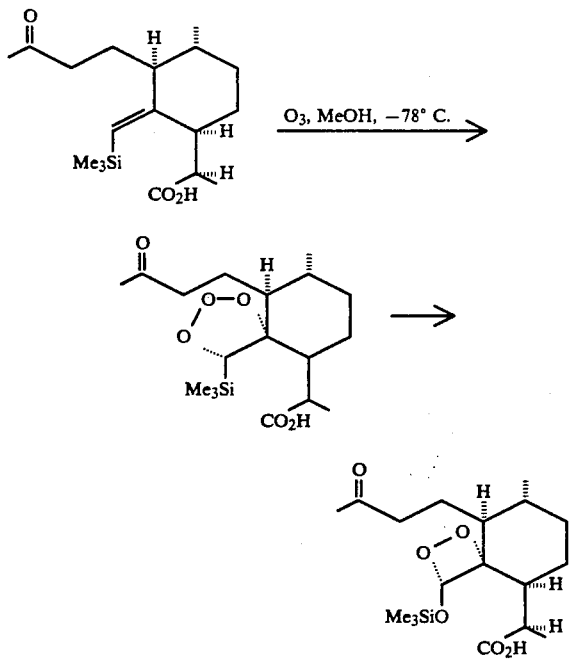

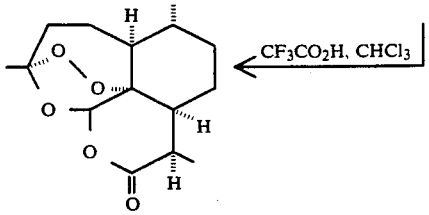

The dioxetane itself is very reactive and unstable. If it is allowed to stand int eh solvent or as a neat solid, it may react and degrade. The dioxetane may undergo a thermal retro [2II+2II] cycloaddition to yield a trialkylsilylformate and a ketone of the base structure 17. This process can be referred to as chemiluminescence, and the rate at which this unwanted decomposition occurs is related to the temperature at which the intermediate is stored as well as intrinsic structural features. Thus, it is generally desired to promptly recover the dioxetane from the solvent. This can be carried out by stripping the solvent off with vacuum or other like processes which minimize the possibility of degradative reaction.

The isolated dioxetane is promptly converted to the desired polyoxa tetracyclic by treatment with acid. This acidification can be carried out in a nonaqueous liquid reaction phase. The acid employed should be of at least moderate strength as shown by a pKa of 5 or less and can be an organic or an inorganic acid. Typical acids include acetic acid and the substituted acetic acids such as trichloro acetic acid and trifluoro acetic acid and the like; other strong organic acids such as alkyl sulfonic acids and the like; the mineral acids such as the hydrohalic acids, e.g. HCl, HBr, etc, the oxyhalo acids such as HClO$_3$ and the like; sulfuric acid and phosphoric acid and the like. The acidification can also be carried out in a biphasic system of aqueous acid and organic solvent.

The organic reaction phase can be any liquid which will be inert and not adversely affect the dioxetane. Halocarbons and halohydrocarbons such as carbon tetrachloride and chloroform are very suitable. Other solvents such as ethers, esters, aromatic hydrocarbons, etc. may be used but alcohols are to be avoided because they can cause unwanted transesterification reactions which decrease the yield of the process.

The rearrangement of the dioxetane is catalyzed by acid, thus in principle only a trace amount of acid is needed. However, the rate of thermal decomposition may compete with acid catalyzed ring opening of the dioxetane. Therefore, to insure that ring opening occurs before thermal decomposition, the use of more than a trace amount of acid is preferred. In particular, the amount of acid added is generally at least about one equivalent based on the amount of dioxetane present. Large excesses are generally not needed and the preferred amount of acid is from about 1 to about 10 and especially from about 1 to about 2 equivalents based on the amount of dioxetane present. This reaction does not require high temperatures. It will go to completion in four hours at room temperature (see Example 14). The reaction may also proceed to completion either more rapidly than 4 hours or more slowly, depending on the acid and solvent system employed. Higher temperatures may be employed if desired and if it is ascertained that they do not give unacceptable yield losses. Temperatures are from about −100° C. to about +50° C. can be used with temperatures of from about −20° C. to about +30° C. being preferred and temperatures of from about 0° C. to about +20° C. being more preferred. As would be expected, times are inversely related to temperature with times in the range of one hour to about 24 hours being useful.

Following the acidification reaction, the solvent and any excess acid can be removed. This can be carried out by evaporation of the solvent and volatile acid under vacuum or in the case of nonvolatile acids, the reaction mixture can be neutralized with aqueous sodium bicarbonate and extracted with organic solvent. The solvent can then be evaporated.

5. The Incorporation of the Ozonolysis into an Overall Synthesis Scheme

The ozonolysis of this invention finds preferred application as part of overall synthetic schemes for producing the desired polyoxa tetracyclics. An example of one of these overall schemes is given in FIGS. 1 and 2 where a scheme for producing arteminisin is shown.

Figure 2:
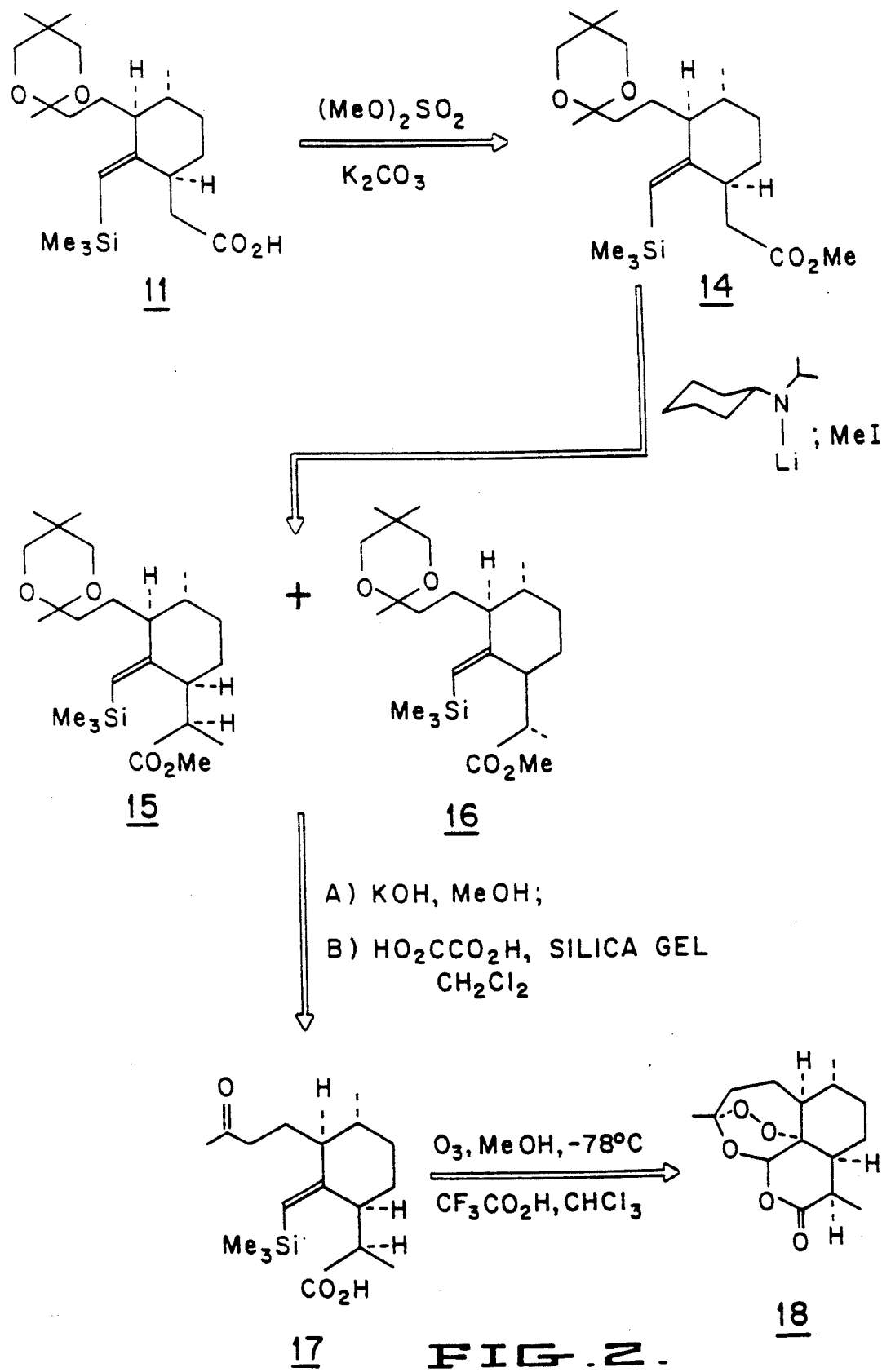
FIG. 2 is a flow diagram showing an alternative sequence of chemical reactions useful in the total synthesis of arteminisin.

The scheme set out in FIGS. 1 and 2 is a stereoselective total synthesis of arteminisin 18 (Qinghaosu) and 13-desmethylartemisinin 13 starting from the known sulfoxide 1 (available from R(+)-pulegone, William R. Roush and Alan E. Walts, *J. Amer. Chem. Soc.* 106, 721 (1984)). Treatment of the dianion derived from 1 with the known bromide 2 afforded a mixture of diastereomeric sulfoxides (3) which was reduced directly in wet THF with aluminum-mercury amalgam to give the ketone 4. The ketone 4 was reacted with p-toluenesulfonylhydrazide to give the hydrazone 5. Reaction of the hydrazone 5 in N,N,N', N'-tetramethylethylenediamine with n-butyllithium and quenching of the resultant vinyl anion with dimethylformamide afforded the unsaturated aldehyde 6.

Straightforward reduction of the aldehyde 6 with diisobutyl-aluminum hydride gave the allylic alcohol 7 which was silylated with trimethylsilyl chloride and imidazole to give the silyl ether 8. Deprotonation of the allylic ether 8 with tert-butyllithium in THF gave the product, from Brook rearrangement product, 9. Acetylation of 9 then gave the acetate 10. Deprotonation of the ester 10 with lithium N-cyclohexyl-N-isopropylamide (LICA) followed by in situ ester-enolate Claisen rearrangement gave the carboxylic acid 11.

The carboxylic acid 11 could be converted to 13-desmethylartemisinin (13) in the following manner. Treatment of 11 with oxalic acid impregnated silica gel gave the keto-acid 12. Ozonolysis of 12 at low temperature in methanol gave an unstable intermediate dioxetane which was treated immediately with $CF_3CO_2H$ in $CDCl_3$ to afford (Scheme I) the nor analog of arteminisin, 13.

Alternatively, (Scheme II, FIG. 2.) 11 could be esterified to give the ester 14 which could be methylated to provide a mixture of monomethylated products, 15 and 16, in a 3:1 ratio respectively. This ester mixture was sequentially treated with KOH in methanol followed by oxalic acid on wet silica gel to provide, after chromatography, the stereoisomerically pure keto-acid 17.

Finally, ozonolysis of 17 in methanol at −78° C. gave an unstable dioxetane intermediate which, after evaporation of the methanol, was treated with dilute moist $CF_3CO_2H$ in $CDCl_3$, affording optically pure arteminisin 18. As will be shown in the Examples, the synthetic material 18 was identical to naturally derived qinghaosu. Such synthetic material would be useful as an antimalarial.

In one important application, this synthetic sequence can be modified slightly to produce radiolabeled arteminisin. This can be carried out effectively and simply by using carbon 14-based $CH_3I$ in the alkylation of compound 14. This will insert the radiolabel at the 13 position where it is stable and nonlabile. The product of this synthesis is of particular usefulness in biological testing of arteminisin where its metabolic fate, absorption and the like can be easily tracked because of the added radiolabel.

As shown in General Formula I., the present invention permits the stereospecific synthesis of many polyoxa tetracyclic compounds beyond arteminisin. In these cases, one could use the synthetic schemes set forth in the Figures with appropriate modifications. For example, to vary $R_1$ from the one carbon alkylene bridge shown in FIGS. 1 and 2 to a two or three carbon bridge by homologating the $-CH_2-COOH$ group in compound 11 or compound 15 to the corresponding higher analogs. The $R_1$ bridge can be substituted with $R^*$ groups by alkylation with $x-R^*$ where x is a leaving group such as a halide (e.g. I or Br) a tosylate, a mesylate or the like. This alkylation can take place before or after the homologation, depending upon the particular site on the $R_1$ group sought to be substituted.

The $R_2$ bridge is set by the ring structure in compound 1. In FIG. 1, compound 1 is shown as a cyclohexanone-based material. One could as well start with cyclopropanone (thereby obtaining a carbon-carbon single bond $R_2$), cyclobutanone (thereby obtaining a $-CH_2-R_2$), cyclopentanone, etc. In every case, the carbons of the starting aldehyde can be substituted with $R^*$ groups as desired on $R_2$.

$R_3$ is determined by the nature of the leaving-group containing side chain in alkylation agent 2 in FIG. 1. Thus, if this side chain is varied in length or substitution, so is $R_3$.

Similarly, $R_4$ can be altered by varying the other substituent on the carbon atom between the two ether oxygens on compound 2. In compound 2 this group is a methyl and $R_4$ is a methyl. If this group is altered to be a hydrogen or an $R^*$ substituted methyl, $R_4$ will follow accordingly.

Figure 3:
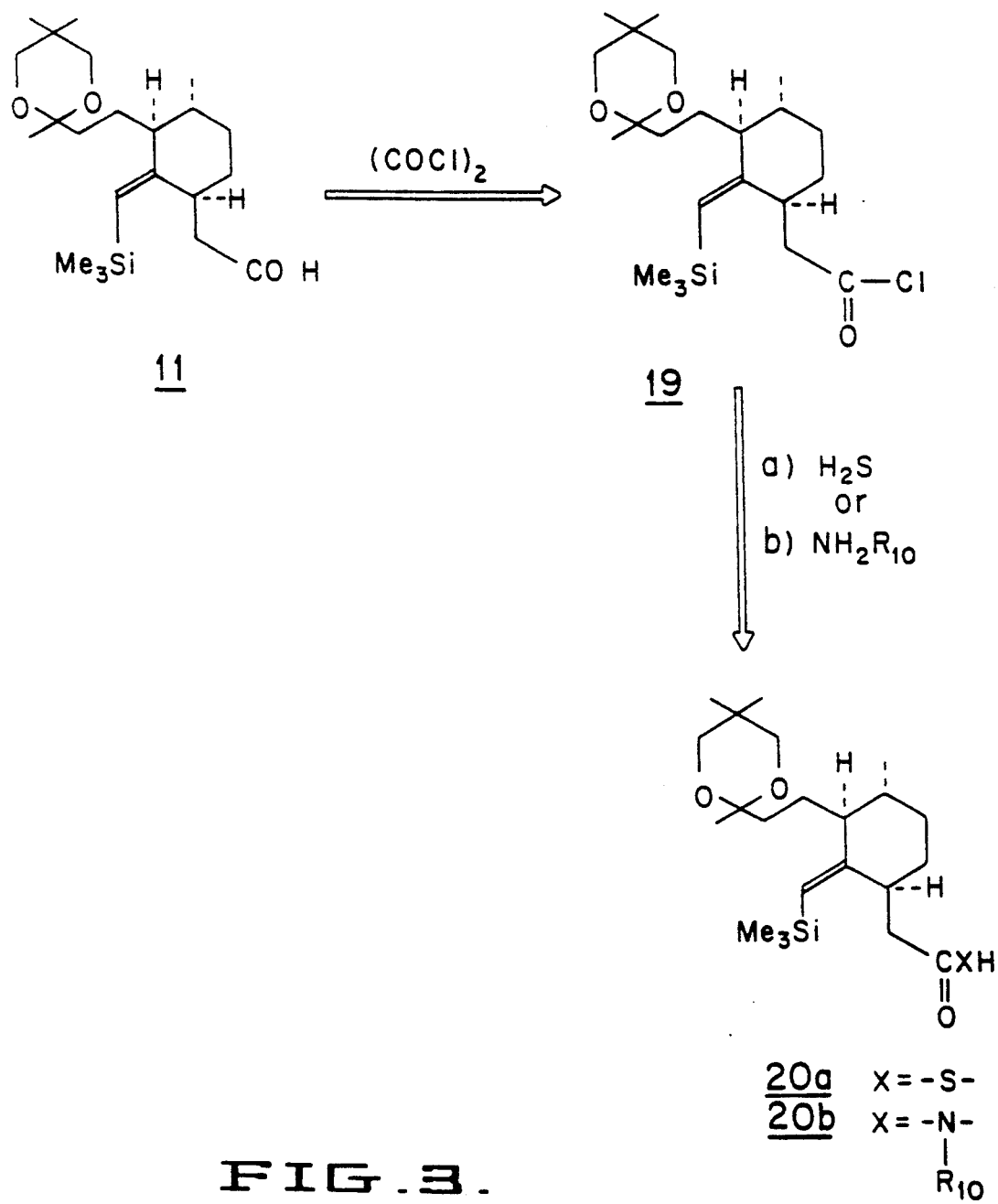
FIGS. 3, 4, and 5 are each a flow diagram showing synthetic routes to a variety of arteminisin analogs.

The preparation schemes set forth in FIGS. 1 and 2 result in products of General Structures 1-4 where X is $-O-$. In FIG. 3, a variation of the scheme of FIG. 1 is depicted which will produce compounds where X is $-S-$ or

The scheme of FIG. 3 begins with acid 11. This material is converted to the acid chloride 19 by conventional treatment with oxalyl chloride ClCOCOCl, thionyl chloride, or the like. Acid chloride 19 can then enter into a nucleophilic substitution with $H_2S$ or the amine $NH_2R_{10}$ to insert an $-S-$ or

as X in compounds 20a and 20b, respectively. These compounds of General Formula II can be further processed by the ozonolysis of the invention to yield corresponding $X=-S-$ and desmethyl materials of General Formula I.

Figure 4:
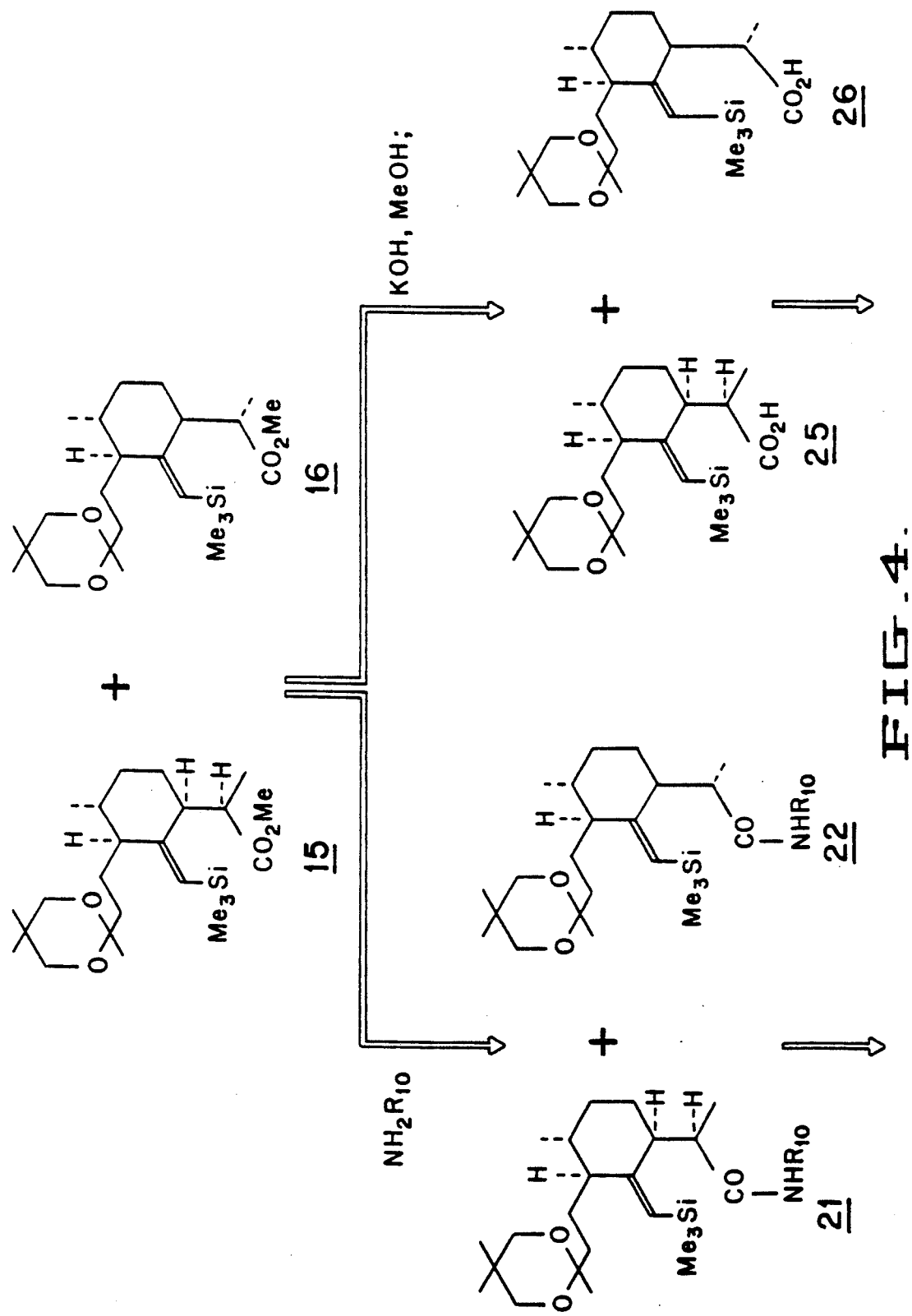
Figure 4:
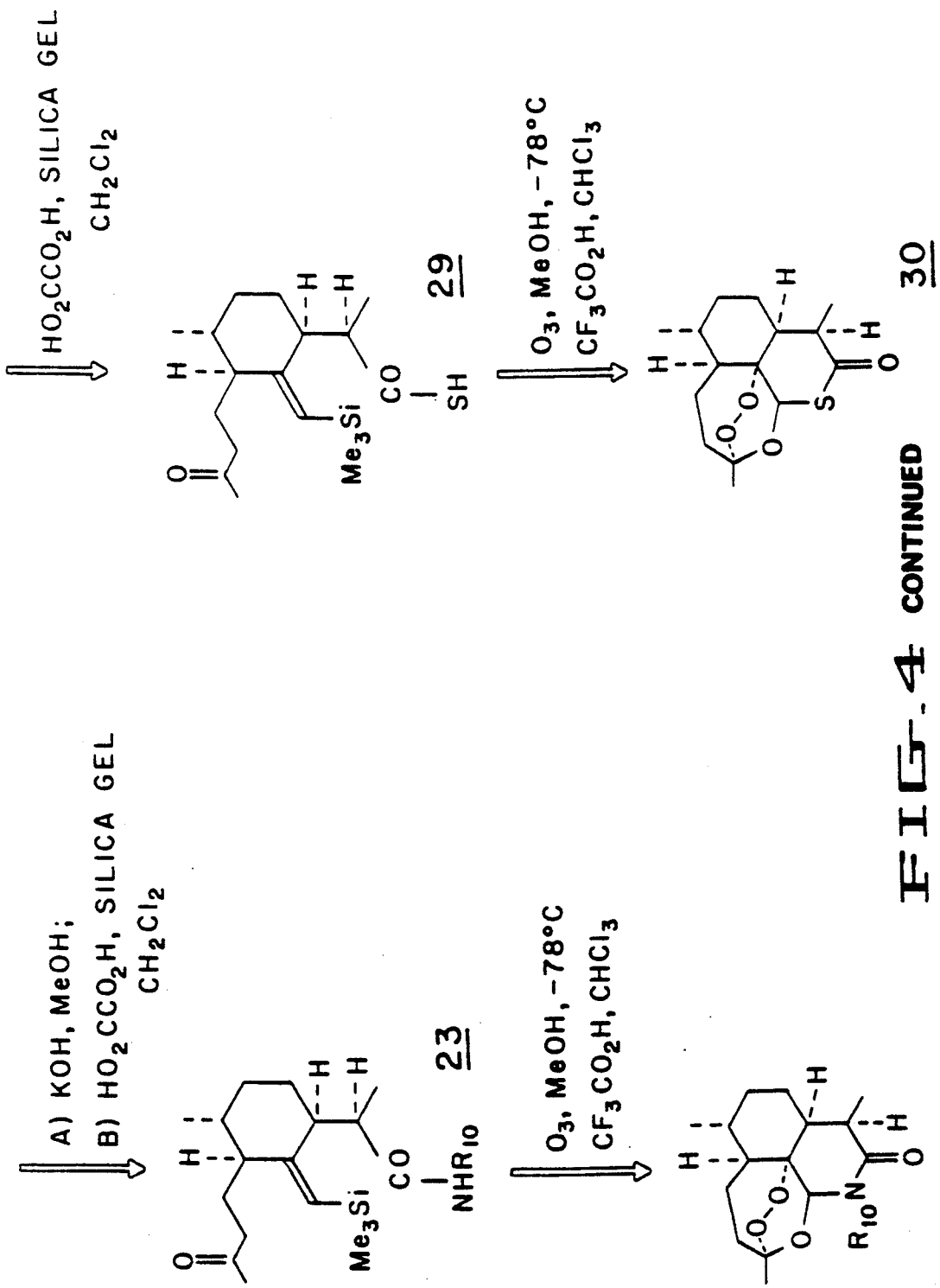

Turning to FIG. 4, a preparation is shown for inserting —S— and

groups into the arteminisin structure. In one scheme, the mixture of esters 15 and 16 produced as in FIG. 2 is contacted with primary amine

to give the mixture of amides 21 and 22. (Alternatively, esters 15/16 can be hydrolyzed with methanolic KOH to the mixture of acids 25 and 26. This mixture can be converted to the corresponding mixed acid chlorides by the method described with FIG. 3 and the acid chlorides reacted with

to give the mixture of amides 21 and 22.

The mixture of amides 21 and 22 is then treated with methanolic base followed by treatment with oxalic acid-impregnated silica gel to yield the keto-amide 23 of the General Formula II. This material is subjected to ozonolysis to yield the $NR_{10}$ analog 24 of arteminisin.

To insert a sulfur X into the structure, the mixed acid chlorides 25 and 26 are reacted with $H_2S$ to yield 27 and 28. When this material is treated with the oxalic acid on silica gel, the sulfur compound 29 of General Formula II is formed. When subjected to ozonolysis, compound 30 of General Formula I results.

$R_5$ and $R_6$ are together a carbonyl oxygen in compounds 13 and 18 in FIGS. 1 and 2. This carbonyl can be reduced, without affecting the reduction-sensitive peroxy group, by the use of sodium borohydride, as reported by M.-m. Liu et al., in Acta Chim. Sinica, Vol. 37, 129 (1979). This reduction converts the carbonyl to a lactol (hemiacetal wherein $R_5$ is H and $R_6$ is OH. The $R_5$ hydrogen can be replaced with $R^*$ group by alkylation with $X-R^*$. An $R_6$ OH can be converted to an ether or ester by art known techniques.

Figure 5:
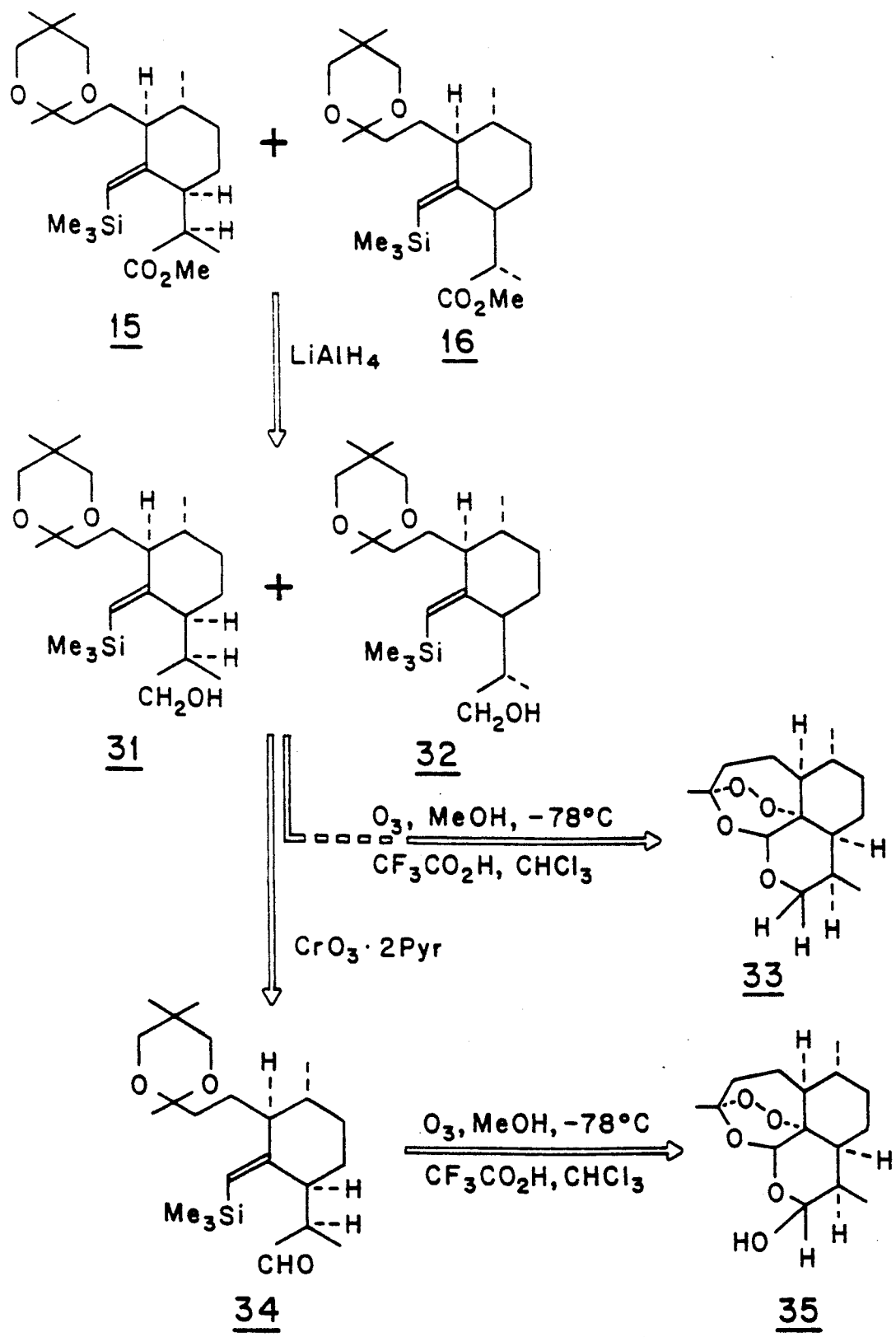
Figure 5:
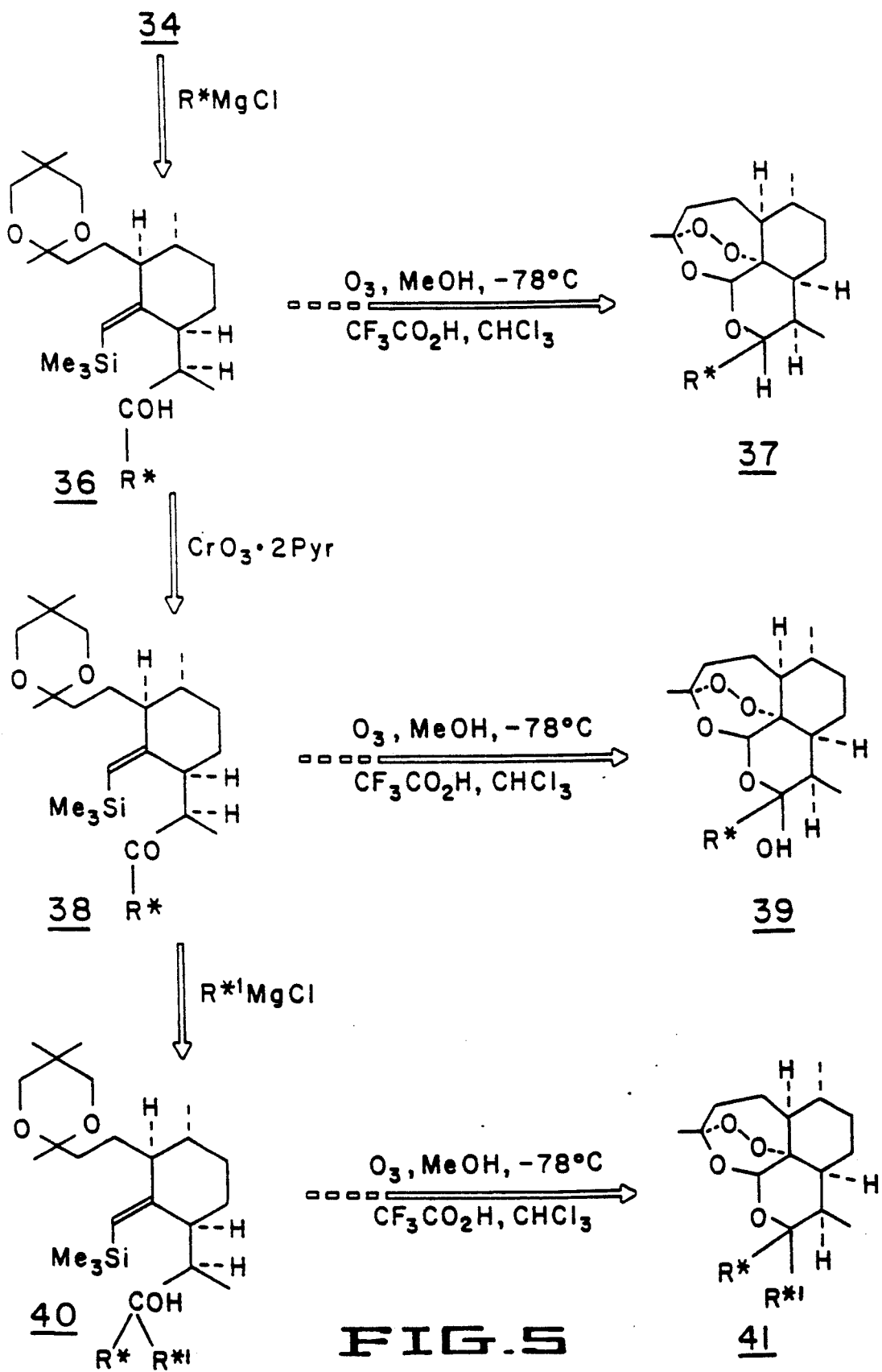

The other possible configuration for $R_5$ and $R_6$ as set forth in General Formula I can be produced as shown in FIG. 5. In each of the five sequences given in FIG. 5, the reaction with oxalic acid to cleave the side chain protection and form the ketone as shown in FIGS. 1, 2, and 4 has been omitted for brevity and replaced by ". . .".

In one of these sequences, the mixed esters 15 and 16 are reduced with lithium aluminum hydride to alcohols 31 and 32. After side-chain deprotection, ozonolysis yields compound 33 where $R_5$ and $R_6$ are hydrogen.

In the next variation, 31 and 32 are oxidized to aldehyde 34 which after deprotection and ozonolysis yields 35 where $R_5$ and $R_6$ equal OH and H.

Aldehyde 34 can be alkylated with Grignard reagent to give alcohol 36. This alcohol can be carried forward to give compound 37 of Formula I, where $R_5$ and $R_6$ are $R^*$ and H.

Alcohol 36 can be oxidized to aldehyde 38. This material can be deprotected and subjected to oxonolysis to give 39 where $R_5$ and $R_6$ are $R^*$ and OH.

In another variation, aldehyde 38 can be treated again with Grignard to add an additional $R^*$ group (the same or different than the $R^*$ of 38), and this product can be deprotected and ozonized to give 40. It will be appreciated that in this last sequence that if the two $R^*$s are identical, one could add them at once to esters 15 and 16 by using excess Grignard reagent.

It will also be appreciated that the reactions of FIG. 5 could be run on the acid chloride of acid compound 11 of FIG. 1 to give the corresponding desmethyl materials.

Because the tetracyclic compounds of this process all contain the peroxy linkage, which can lead to free radical intermediates in vivo, they should have antiprotozoan activities against a broad range of parasites such as Toxoplasma, Leishmania, Trypanosoma, etc, in addition to Plasmodia. They should also have antihelmenthic activity against such diseases as Schistosoma and Trichinella, etc. (R. Docampo et al., *Free Radicals in Biology*, Vol. VI, Chapter 8, p. 243, 1984, Academic Press, Inc.).

This peroxide link and the free radicals it can produce are useful in a range of industrial chemical settings, as well.

6. Examples

The present invention will be further illustrated by the following Examples. These are presented solely to illustrate preferred modes for carrying out this invention. They are not to be construed as limiting its scope which is instead determined solely by the appended claims.

These examples relate to the preparation of arteminisin and make reference to the reaction schemes set forth in FIGS. 1 and 2. When compounds are identified by number in these examples, these are the numbers appearing in these Figures.

EXAMPLE 1

2,5,5-Trimethyl-2-(2'-(1"R-methyl-3"-oxocyclohex-2"-yl)-ethyl-1,3-dioxane (4)

5R-Methyl-2-phenylsulfinylcyclohexanone (1) (7.14 g, 30.0 mmoles) in dry THF (75 ml) at $-30°$ C. under argon was treated with a solution of lithium diisopropylamide (prepared from 9 ml or 64.5 mmoles of diisopropylamine and 41.6 ml of 1.55M solution of n-BuLi in hexane) in dry THF (75 ml) followed by dry hexamethylphosphoramide (HMPA) (30 ml). The mixture was stirred at $-30°$ C. for 3 hr and then 2-(2'bromoethyl)-2,5,5-trimethyl-1,3-dioxane (2) (8.42 ml. 36.0 mmoles) was added dropwise via syringe. The mixture was stirred at $-30°$ C. for 1 hr and then was allowed to warm to room temperature over 1 hr. The mixture was poured into ice-cold, saturated ammonium chloride solution (100 ml)and was extracted with diethyl ether (2×100 ml). The organic layers were washed with water (3×100 ml) and brine (100 ml), dried (MgSO4), and evaporated in vacuo to give 15.1 g of crude alkylation product (3). This was dissolved in THF (675 ml) to which was added water (75 ml) followed by 7.5 g of amalgamated aluminum foil strips (prepared by dipping aluminum foil strips in 2% aqueous mercuric chloride for 15 sec followed by washing with absolute ethanol and diethyl ether). The mixture was stirred at room temperature for 2 hr and then was filtered under reduced pressure while the solids were being washed with diethyl ether (500 ml). The filtrate was washed with 5% sodium hydroxide solution (3×500 ml), water (500 ml), and brine (500 ml). The aqueous phases were sequentially extracted with diethyl ether (500 ml) and the combined organic phases were dried (MgSO$_4$) and evaporated in vacuo to give 10.35 g of crude material. This was purified by flash chromatography on 207 g silica gel 60 (230-240 mesh), eluting with EtOAc/hexane (10:90)→(15:85) to give the product 4 (4.0 g, 50%) as a colorless oil. IR (thin film): 2960 (s), 2940 (m), 2880 (m), 1716 (s) cm$^{-1}$. NMR (400 MHz, CDCl$_3$): δ3.501 (1H, d, J 11 Hz), 3.496 (1H, d, J 11 Hz), 3.454 (1H, d, J, 11 Hz), 3,450 (1H, d, J 11 Hz), 2.30 (3 H, m) 2.01 (2 H, m), 1.83 (1H, m), 1.65 (6 H, m), 1.34 (3 H, s), 1.03 (3 H, d, J 7 Hz), 0.93 (6 H, s). C$_{13}$NMR (400 MHz, CDCl$_3$): δ213.2, 99.1, 70.5, 70.3, 57.1, 41.6, 41.4, 38.4, 33.5, 33.3, 29.9, 25.6, 22.7, 21.7, 20.8, 20.5. MS (m/e): 268 (M+), 253 (M-Me). Analysis: Found: C, 71.73; H, 10.33. C$_{16}$H$_{28}$O$_3$ requires C, 71.64; H, 10.45%

EXAMPLE 2

2,5,5-Trimethyl-2-[2'-(1"R-methyl-3"-oxocyclohex-2"-yl) -ethyl]-1,3-dioxane p-tosylhydrazone (5)

A mixture of the ketone (4) (3.60 g, 13.44 mmoles), dry THF (100 ml), p-tosylhydrazine (2.49 g, 13.44 mmoles), and pyridine allowed to cool and then was evaporated in vacuo, giving 8.5 g of crude material. This was purified by flash chromatography on 170 g silica gel 60 (230-400 mesh) and elution with EtOAc/hexane (25:75)→(40:60) to give the produce 5 (5.5 g, 94%) as a gummy solid. IR (CHCl$_3$): 3120 (m), 2955 (s), 2875 (s) 1735 (m), 1635 (2), 1605 (w), 1500 (w) cm$^{-1}$. NMR (CDCl$_3$): δ8.53 (1H, broad), 7.81 (2H, d, J 8 Hz), 7.20 (2H, d, J 8 Hz), 3.44 (4H, s), 2.39 (3H, s), 2.19 (3H, m), 1.54 (8H, m), 1.27 (3H, s), 1.24 (3H, d, J 5 Hz), 0.97 (3H, s), 0.93 (3H, s). MS (m/e): 437 (M+H+), 421 (M-Me).

EXAMPLE 3

2,5,5-Trimethyl-2-[2'(1"R-methyl-3"-3"-formylcyclohex-3"-en-2"-yl) -ethyl]-1,3-dioxane (6)

To a solution of the hydrazone (5) (220 mg, 0.505 mmole) in dry TMEDA (10 ml) at −20° C. under argon was added n-BuLi (1.30 ml of 1.55M solution in hexane, 2.02 mmoles). The mixture was stirred at room temperature for 30 min and then was cooled to 0° C. After addition of dry DMF (0.5 ml), by drops, the mixture was stirred at 0° C. for 30 min and then was poured into ice-cold saturated ammonium chloride solution (20 ml). This was extracted with ethyl acetate (2×20 ml) and washed with saturated ammonium chloride solution (20 ml), water (20 ml), and brine (20 ml). The combined organic extracts wee dried (Na$_2$SO$_4$) and evaporated in vacuo to give 175 mg of crude material, which was purified by preparative TLC, eluting with EtOAc/hexane (15:85), to give the product 6 (77 mg, 55%) as a pale yellow oil. IR (thin film): 2960 (s), 2870 (m), 2710 (w), 1685 (s), 1635 (w) cm$^{-1}$. NMR (400 MHz, CDCl$_3$): δ9.38 (1H, s), 6.73 (1H, t, J r Hz), 3.472 (1H, d, J 11 Hz), 2.28 (2H, m), 1.91 (1H, m), 1.71 (5H, m), 1.39 (2H, m), 1.31 (3H, s), 0.94 (3H, s), 0.89 (3H, s), 0.86 (3H, d, J 7 Hz). C$_{13}$NMR (400 MHz, CDCl$_3$): δ194.7, 151.2, 99.0, 70.3, 41.6, 37.7, 35.0, 29.9, 28.5, 27.5, 26.1, 23.9, 23.0, 22.7, 21.0, 18.6, 14.1. MS (m/e): (M-Me).

EXAMPLE 4

2,5,5-Trimethyl-2-(2'-(1"R-methyl-3"-hydroxymethylcyclohex-3"-en-2"-yl)-ethyl) -1,3-dioxane (7)

The aldehyde (6) (1.1 g, 4.04 mmoles) in dry THF (10 ml) was added dropwise via syringe to diisobutylaluminum hydride (DIBAL) (4.21 ml of 1.2M solution to toluene, 5.05 mmoles ) in dry THF (30 ml) at −78° C. under argon. The mixture was stirred at −78° C. for 30 min. and then allowed to warm to room temperature over 30 min. The mixture was poured into ice-cold, saturated potassium sodium tartrate solution (50 ml) and was extracted with ethyl acetate (2×50 ml). The organic extracts were washed with saturated potassium sodium tartrate solution, dried (MgSO$_4$), and evaporated in vacuo to give the produce 7 (1.14 g, 100%) as a colorless oil. IR (CHCl$_3$): 3580 (m), 3430 (m, broad), 2990 (s), 2945 (s), 2915 (s), 2855 (s), 1660 (w) cm$^{-1}$. NMR (CDCl$_3$): δ5.68 (1H, m), 3.99 (2H, s), 3.53 (2H, d, J 11 Hz), 3.35 (2H, d, J 11 Hz), 1.94 (3H, m), 1.61 (8H, m), 1.30 (3H, s), 0.98 (3H, s), 0.88 (3H, d, J 6 Hz), 0.81 (3H, s). MS (m/e): 267 (M-Me). Analysis: Found: C, 72.60; H, 10.53. C$_{17}$H$_{30}$O$_3$ requires C, 72.34; H, 10.64%.

EXAMPLE 5

2,5,5-Trimethyl-2-(2'-(1"R-methyl-3"-trimethylsilyloxymethylcyclohex-3"-en-2"-yl)-ethyl)-1,3-dioxane (8)

To the alcohol 7 (100 mg, 0.355 mmole) in dry DMF (4 ml) at 0° C. under argon was added imidazole (242 mg, 3.55 mmoles) and trimethylchlorosilane (116 mg, 1.065 mmole). The mixture was stirred at 0° C. for 1 hr, then poured into ice-cold water (20 ml) and extracted with diethyl ether (2×20 ml). The organic extracts were washed with water (20 ml) and brine (20 ml), dried (MgSO$_4$), and evaporated in vacuo to give the product 8 (126 mg, 100%) as a colorless oil. 1R (CHCl$_3$): 3000 (s), 2950 (s), 2920 (s), 2860 (s) cm$^{-1}$. NMR (CDCl$_3$): δ5.60 (1H, m), 3.98 (2H, s), 3.48 (2H, d, J 11 Hz), 3.32 (2H, d, J 11 Hz), 1.92 (3H, m), 1.54 (7H, m), 1.25 (3H, s), 0.92 (3H, s), 0.85 (3H, d, J 7 Hz), 0.80 (3H, s), 0.05 (9H, s). MS (m/e): 354 (M+), 339 (M-Me).

EXAMPLE 6

2,5,5-Trimethyl-2-(2'-(1"R-methyl-3Δ-trimethylsilylhydroxymethylcyclohex-3"-en -2"-yl)-ethyl)-1,3-dioxane (9)

To a solution of the silyl ether 8 (7.20 g, 20.3 mmoles) in dry THF (100 ml) at −78° C. under argon was added t-BuLi (23.9 ml of 1.7M solution in pentane, 40.6 mmoles). The mixture was stirred at −30° to −40° C. for 2½ hr and then was recooled to −78° C. A mixture of acetic acid (15 ml) and THF (50 ml) was added slowly and the resulting mixture was poured into ice-cold, saturated sodium bicarbonate solution (200 ml). This was extracted with chloroform (3×200 ml) and washed with brine (200 ml). The combined organic extracts were dried (MgSO$_4$) and evaporated in vacuo to give 8.20 g of crude material. This was purified by flash chromatography on 246 g silica gel 60 (230-400 mesh), eluting with EtOAc/hexane (10:90)→(30:70) to give the product 9 (2.60 g, 36%) as well as the alcohol 7 (2.50 g, 44%). IR (CHCl$_3$): 3550 (w, broad), 3000 (s), 2955 (s), 2935 (s), 2870 (s) cm$^{-1}$. NMR (CDCl$_3$): δ5.53 (1H, m), 3.84 (1H, m), 3.57 (2H, d, J 11 Hz), 3.37 (2H, d, J 11 Hz), 2.01 (3H, m), 1.63 (8H, m), 1.34 (3H, s), 1.01 (3H, s), 0.92 (3H, d, J 7 Hz), 0.85 (3H, s), 0.04 (9H, s). MS (m/e): 354 (M+), 353 (M-H), 337 (M-OH). Analysis: Found: C, 66.02; H, 10.58; Si, 6.87. $C_{20}H_{38}SiO_3 \cdot \frac{1}{2}EtOAc$ requires C, 66.33; H, 10.55; Si, 7.04%.

EXAMPLE 7

2,5,5-Trimethyl-2-(2'-(1"R-methyl-3"-trimethylsilyel-hydroxymethylcyclohex-3"-en -2"-yl)-ethyl)-1,3-dioxane acetate ester (10)

To a solution of the alcohol 9 (354 mg, 1.00 mmole) in diethyl ether (10 ml) at room temperature under argon was added dry pyridine (0.17 ml), 2.00 mmoles), acetic anhydride (0.14 ml, 1.50 mmole), and 4-dimethylaminopyridine (10 mg). The mixture was stirred at room temperature for 16 hr and then was poured into ice-cold water (20 ml). This was extracted with diethyl ether (2×20 ml). The combined organic layers were dried (MgSO4) and evaporated in vacuo to give the product 10 (376 mg, 95%) as a colorless oil. IR (CHCl3): 3000 (m), 2960 (s), 2930 (s), 2875 (s), 1725 (s), 1645 (w) cm$^{-1}$. NMR (CDCl3): $\delta$5.34 (1H, m), 5.08 (1H, m), 3.40 (4H, m), 2.06 (3H, s), 2.05–1.20 (10H, m), 1.35 (3H, s), 1.01 (3H, s), 0.88 (6H, m), 0.01 (9H, s). MS (m/e): 396 (M+), 395 (M-H). Analysis: Found: C, 65.24; H, 10.13. $C_{22}H_{40}SiO_4 \cdot \frac{1}{2}H_2O$ requires C, 65.19; H, 10.12%.

EXAMPLE 8

2,5,5-Trimethyl-2-(2'-(4"-carboxymethyl-1"R-methyl-3"-trimethylsilylmethylenecyclohex -2"-yl)-ethyl)-1,3-dioxane (11)

To freshly distilled dry cyclohexylisopropylamine (0.51 ml, 3.076 mmole) in dry distilled THF (5 ml) at 0° C. under argon was added n-BuLi (1.92 ml of 1.6M solution in hexane, 3.076 mmoles). The mixture was stirred at 0° C. for 10 min. and then was cooled to −78° C. The ester 10 (609 mg, 1.538 mmole) in dry distilled THF (5 ml) was added dropwise over 30 min and the mixture was stirred at −78° C. for 3 hr followed by room temperature for 4 days. Then the mixture was poured into ice-cold, saturated ammonium chloride solution (20 ml) with 38 drops of 5N hydrochloric acid, and extracted with chloroform (3×20 ml). The organic extracts were washed with brine (20 ml), dried (MgSO4), and evaporated in vacuo to give 754 mg of crude material. This was purified by flash chromatography on 76 g silica gel 60 (230–400 mesh), eluting with (1% HOAc/EtOAc)//hexane (7:93)→(50:50) to give the product 11 (361 mg, 59%). IR (CHCl3): 3575 (w), 3030 (w, broad), 3000 (m), 2955 (s), 2870 (m), 1710 (s), 1610 (w) cm$^{-1}$. NMR (CDCl3): $\delta$8.17 (1H, broad), 5.21 (1H, s), 3.28 (4H, m), 2.38 (2H, m), 2.00–100 (11H, m), 1.12 (3H, s), 0.75 (9H, m), −0.12 (9H, s). MS (m/e): 396 (M+), 381 (M-Me). High-resolution MS: Found: 396.270. $C_{22}H_{40}SiO_4$ requires 396.269.

EXAMPLE 9

4R-Methyl-3-(3'-oxobutyl)-2-trimethylsilylmethylenecyclohex-1-ylacetic acid (12)

To silica gel 60 (70–230 mesh, 400 mg) in dichloromethane (4 ml) was added 10% aqueous oxalic acid (4 drops), with stirring. The mixture was stirred at room temperature for 5 min. Then the ketal 11 (150 mg, 0.38 mmole) in dichloromethane (4 ml) was added and the mixture was stirred for a further 6 hr. The mixture was filtered under suction while the solid was being washed with dichloromethane (8 ml). The filtrate was evaporated in vacuo to give 131 mg of crude material. This was purified by flash chromatography on 13 g silica gel 60 (230–400 mesh), eluting with (1% HOAc/EtOAc)-/hexane (50:50)→(90:10) to give the product 12 (77 mg, 65%) as a solid. IR (CHCl3): 3580 (w), 3040 (m, broad), 2970 (s), 1710 (s), 1610 (m) cm$^{-1}$. NMR (CDCl3): $\delta$8.53 (1H, broad), 54.0 (1H, s), 2.70 (1H, m), 2.47 (5H, m), 2.10 (3H, s), 1.75 (7H, m), 0.85 (3H, d, J 7 Hz), 0.03 (9H, s). MS (m/e): 310 (M+), 295 (M-Me), 277 (M-Me-H2O). High-resolution MS: Found: 310.197. $C_{17}H_{30}SiO_3$ requires 310.196.

EXAMPLE 10

13-desmethylartemisinin (13)

Ozonized oxygen (7.0 psi, 0.4 L/min. 70 V) was bubbled through a sintered-glass frit into a solution of the ketone 12 (77 mg, 0.248 mmole) in dry methanol (20 ml) at −70° C. for 68 seconds. The mixture was evaporated in vacuo to give 84 mg of material, which was dissolved in deuterochloroform (0.4 ml) in an NMR tube. Ten drops of a ten percent solution of trifluoroacetic acid in deuterochloroform were added and the mixture was kept at room temperature for 5 hr followed by 4° C. for 16 hr followed by room temperature for 6 hr. The mixture was purified by flash filtration on 7.7 g silica gel 60 (230–400 mesh) covered with a layer of sodium bicarbonate, eluting with EtOAc/CHCl3 (10:90) to give 13-desmethylartemisinin (13) (26 mg, 39%). IR (CHCl3): 2990 (w), 2950 (m), 2920 (m), 2855 (m), 1735 (s) cm$^{-1}$. 400 MHz NMR (CDCl3): $\delta$5.89 (1H, s), 3.18 (1H, dd, J 7, 18 Hz), 2.40 (1H, ddd, J 4, 11, 13 Hz), 2.25 (1H, dd, J 1, 18 Hz), 2.02 (1H, m), 1.87 (1H, m) 1.83 (1H, m), 1.66 (2H, m), 1.45 (3H, s), 1.33 (5H, m), 0.99 (3H, d, J 5 Hz). MS (m/e): 268 (M+), 253 (M-Me).

EXAMPLE 11

2,5,5-Trimethyl-2-(2'-(4"-carbomethoxymethyl-1"R-methyl-3"-trimethylsilylmethylenecyclohex -2"-yl)-ethyl)-1,3-dioxane (14)

To the carboxylic acid 11 (59 mg, 0.149 mmole) in dry acetone (5 ml) was added powdered anhydrous potassium carbonate (21 mg, 0.15 mmole) followed by dimethyl sulfate (14 $\mu$l, 0.15 mmole). The mixture was heated under reflux for 3 hr, then poured into ice-cold 0.1M sodium carbonate solution (20 ml) and extracted with diethyl ether (2×20 ml). The organic extracts were washed with brine (20 ml), dried (m/Mg SO4), and evaporated in vacuo to give 57 mg of crude material. This was purified by preparative TLC, eluting with EtOAc/hexane (10:90) to give the product 14 (39 mg, 64%). NMR (CDCl3): $\delta$5.30 (1H, s), 3,58 (3H, s).

EXAMPLE 12

2,5,5-Trimethyl-2-(2'-4"-(1"'-carbomethyloxyethyl)-1"R-methyl-3"-trimethylsilylmethylenecyclohex-2"-yl)-ethyl)-1,3-dioxane (15/16)

To a solution of dry THF (3 ml) and dry isopropylcyclohexylamine (280 $\mu$l or 1.697 $\mu$mol) under argon at 0°–5° C. was added n-butyllithium (1.6M in hexane, 1.06 ml, or 1.697 mmol). After 10 min at 0°–5° C., 400 $\mu$l of the resultant lithium amide solution (0.24 mmol) was added to a 0° C. solution of the ester 14 (35 mg or 0.0854 mmol) in dry THF (1 ml). After 1 hr at 0° C., the ester enolate solution was treated with CH3I (30 $\mu$l or 0.482 mmole). After 1 hr at 0° C., the reaction mixture was poured into saturated aqueous NH₄Cl (30 ml) and extracted 2×25 ml EtOAc. The combined organic layer was washed 1×20 ml H₂O, dried over anhydrous MgSO₄, filtered, and the solvent removed on a rotovap. The residual glass was chromatographed on a TLC plate (250 micron, silica gel) with 10% Et₂O-pentane to afford a 3:1 mixture of 15:16 (respectively) as a clear glass, 25 mg or 69% yield. NMR (400 MHz, CDCl₃): δ5.30 (s, 1H), 3.5 (s, 3H), 3.5 (m, 1H), 1:33 (s, 3H), 1.05 (d, J=6.8 Hz, 3 h), 0.98 (s, 3H), 0.91 (d J=7.2 Hz, 3H), 0.87 (s, 3H), 0.090 (s, 9H).

EXAMPLE 13

3S-(3'-oxobutyl)-2-trimethylsilylmethylene-1R, 4R, 7S-menthan-8-oic acid (17)

To a solution of the ester 15/16 (21 mg or 0.495 mmole) dissolved in reagent grade methanol (3 ml) under argon at room temperature was added 10% aqueous KOH (20 μl). The mixture was refluxed until the hydrolysis was complete (about 6 hrs, as determined by TLC). The reaction mixture was cooled to room temperature and poured into 1% aqueous HOAc (25 ml) and extracted 3×20 ml EtOAc. The combined organic layer was washed 2×15 ml H₂O, dried over anhydrous MgSO₄, filtered and the solvent removed on a rotovap. The resultant crude acid was dissolved in CH₂Cl₂ (about 0.5 ml) and added to a well-stirred slurry of silica gel, (50 mg, 70-230 mesh Keiselgel 60) in CH₂Cl₂ (0.5 ml) which had been treated with 10% aqueous oxalic acid (20 μl). After 18 hrs at room temperature under argon, the slurry was filtered and washed with CH₂Cl₂ (10 ml). The solvent was evaporated to give the crude acid 17 (21 mg). The crude acid was purified on a TLC plate (250 micron, silica gel) eluting with 40% EtOAc/hexane (containing 0.4% HOAc). This gave 17 (13 mg or 81% yield) with about 25% isomeric contamination (the 7R analog). The isomeric acid mixture was rechromatographed as before and pure 17 was isolated as a white solid (8.4 mg or 52% overall yield from 15/16). NMR (400 MHz, CDCl₃): δ5.35 (s, 1H), 2.73 (dq, J=6.8, 12 Hz, 1H), 2.3-2.6 (m, 3 H), 2.13 (s, 3H), 1.0 (d, J=7.2 Hz, 3H), 0.92 (d, J =6.8 Hz, 3H), 0.087 (s, 9H).

EXAMPLE 14

Artemisinin (18)

The keto-acid 17 (3.5 mg or 0.0108 mmol) was dissolved in dry methanol (1 ml) and placed in a 1 dram vial under argon with a screw cap. The solution was cooled at −78° C., the cap removed, and a stream of O₃/O₂ (7 psi. 0.4 1/min, 70 v) was bubbled in until a faint blue color was seen (about 10 sec.). The cap was replaced and the solution stood at −78° C. for 5 min. The solution was then purged with argon (5 min.) and warmed to room temperature. The solvent was carefully removed under high vacuum (0.02 mm Hg)), and the resultant solid was kept under high vacuum for 30 min. This product was dissolved in CDCl₃ (0.75 ml) and CF₃CO₂H (10 μl) was added. The mixture was kept at room temperature for 4 hrs and then at −20° C. for 18 hrs. The reaction mixture was evaporated to dryness under high vacuum and then chromatographed on TLC (250 micron, silica gel) with 20% EtOAc/hexane to give pure 18 (1 mg or 33% yield). The synthetic 18 was identical, by proton and carbon NMR (400 MHz), to authentic materials. It was also identical by TLC in several solvent systems.

What is claimed is:

1. A polyoxa tetracyclic compound of the formula

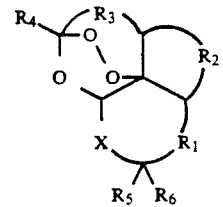

wherein $R_1$ is a one carbon atom long through two carbon atom long alkylene bridge containing from zero up to one lower alkyl substituent, $R_2$ is a three carbon atom long through five carbon atom long alkylene bridge containing from zero up to two lower alkyl substituents, $R_3$ is a one carbon atom through three carbon atom long alkylene bridge bridging the 1 and 4 positions in the formula having from zero up to two lower alkyl substituents on the carbon atom adjacent to the 4 position, $R_4$ is selected from the group consisting of hydrogen, methyl and lower alkyl substituted methyl, $R_5$ and $R_6$ are selected such that they together are a carbonyl oxygen or separately $R_5$ is selected from the group consisting of hydrogen, methyl and lower-alkyl substituted methyl and $R_6$ is selected from the group consisting of hydrogen, hydroxyl, alkyloxy, hydroxycarbonyloxy, alkylaminocarbonyl, alkylaminocarbonyloxy, and ureido, and X is a heteroatom group selected from —O—, —S— and

wherein $R_{10}$ is selected from the group consisting of hydrogen and lower alkyl.

2. The polyoxa tetracyclic compound of claim 1 wherein $R_1$ is a one to two carbon atom long alkylene.

3. The polyoxa tetracyclic compound of claim 1 wherein $R_2$ is a three to five carbon atom long alkylene.

4. The polyoxa tetracyclic compound of claim 1 wherein $R_3$ is a one to two carbon atom long alkylene.

5. The polyoxa tetracyclic compound of claim 1 wherein $R_4$ is a methyl.

6. The polyoxa tetracyclic compound of claim 1 wherein $R_5$ and $R_6$ together are a carbonyl oxygen.

7. A polyoxa tetracyclic compound of the formula

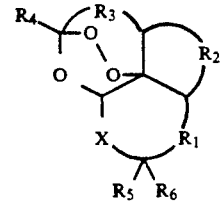

wherein $R_1$ is a one carbon atom long through two carbon atom long alkylene bridge containing from zero up to one lower alkyl substituent, $R_2$ is a three carbon atom long through five carbon atom long alkylene bridge containing from zero up to two lower alkyl substituents, $R_3$ is a one carbon atom long through three carbon atom long alkylene bridge bridging the 1 and 4 positions in the formula having from zero up to two lower alkyl substituents on the carbon atom adjacent to the 4 position, $R_4$ is selected form the group consisting of hydrogen, methyl and lower alkyl substituted methyl, $R_5$ is hydrogen, $R_6$ is hydroxyl, and X is a heteroatom group selected form —O—, —S— and

wherein $R_{10}$ is selected from the group consisting of hydrogen, and lower alkyl.

8. Radiolabelled artemisinin, wherein the radiolabel is present in the 13 position methyl group.

* * * * *